| United States Patent [19] | [11] Patent Number: 4,659,693 |
|---|---|
| Nestor | [45] Date of Patent: Apr. 21, 1987 |

[54] N,N'-DIALKYL SUBSTITUTED GUANIDINO AMINO ACYL RESIDUE SUBSTITUTED GRF-ANALOG PEPTIDES

[75] Inventor: John J. Nestor, San Jose, Calif.

[73] Assignee: Syntex (U.S.A.) Inc., Palo Alto, Calif.

[21] Appl. No.: 707,007

[22] Filed: Feb. 28, 1985

Related U.S. Application Data

[63] Continuation-in-part of Ser. No. 605,346, Apr. 30, 1984, abandoned.

[51] Int. Cl.$^4$ .................. A61K 37/43; C07K 7/10; C07K 7/08
[52] U.S. Cl. ........................... 514/12; 514/13; 530/324; 530/325; 530/326
[58] Field of Search .................. 260/112.5 R; 514/12, 514/13; 530/324, 325, 326

[56] References Cited

U.S. PATENT DOCUMENTS 3,773,919 11/1973 Boswell et al. .................... 424/19
4,118,483 10/1978 König et al. ................. 260/112.5 LH
4,218,474 8/1980 Barnish et al. ...................... 424/177

OTHER PUBLICATIONS

Ling et al., 65*th Annual Endocrine Society Meeting*, 295, 154, 1983.
Rivier et al., 8*th American Peptide Symposium*, Tucson, Arizona, May 22–27, p. 237, 1983.
Ech et al., *Biochemical and Biophysical Research Communications*, 117, 772–779 (1983).
Guillemin et al., "Science, 218, 585–587 (1982).
Journal of Exper. Zoology 231:161–63 (1984).

*Primary Examiner*—Delbert R. Phillips
*Attorney, Agent, or Firm*—Annette M. Moore; Tom M. Moran

[57] ABSTRACT

Peptides which promote the release of growth hormone by the pituitary gland or which inhibit the release of growth hormone by growth hormone releasing factor and which have an N,N'-dialkyl substituted guanidino amino acyl residue at position 1 or 2 are disclosed herein.

26 Claims, No Drawings and when $R_1$=D or L Tyr, Nme Tyr or His, $R_2$ may not be D or L Ala or Leu;

$R_3$ is Asp, Asn or Glu; $R_4$ is Ala or Gly; $R_8$ is Asn or Ser; $R_{10}$ is D or L-Tyr or Phe; $R_{12}$ is Lys or Arg; $R_{13}$ is Ile or Val; $R_{15}$ is Gly or D-Ala; $R_{18}$ is Ser or Tyr; $R_{24}$ is Gln or His; $R_{25}$ is Glu or Asp; $R_{27}$ is D or L-Ala, D or L-Nle, D or L-Ile, D or L-Leu, D or L-Met, or D or L-Val; $R_{28}$ is Asn, Ser or D-Ala; $R_{34}$ is Arg, Ser or Ala; $R_{38}$ is Gln, Arg or Ser; $R_{39}$ is Arg or Gly; $R_{40}$ is Ala, Ser, Arg or Des-$R_{40}$; $R_{41}$ is Arg, Phe, Lys or Y; $R_{42}$ is Val, Phe, Ala, Gln, Gly, Ile, Leu, Lyr, Pro or Y; $R_{43}$ is Asn, Arg or Y; and $R_{44}$ is Leu, or Y wherein Y is OH or NH.

These peptides can be used to promote the growth of warm-blooded animals, particularly humans, cattle, sheep, pigs, and fowl (especially chickens and turkeys) and of cold-blooded animals in aquaculture. These peptides can also be used increase milk production in lactating animals. GRF-analog fragments and pharmaceutically acceptable non-toxic salts of the foregoing compounds also fall within the scope of this invention.

In addition, when $R_1$=H, the resultant analogs are competitive inhibitors of GRF and may be used as diagnostic agents to diagnose the presence of GRF producing tumors.

This invention also relates to pharmaceutical and veterinary compositions comprising one or more GRF-analog peptides, or non-toxic salts of the foregoing, dispersed in a pharmaceutically or veterinary acceptable excipient.

DETAILED DESCRIPTION OF THE INVENTION

Abbreviations and Definitions

The conventional abbreviations for the various common amino acids are used as generally accepted in the peptide art as recommended by the IUPAC-IUB Commission on Biochemical Nomenclature, *Biochemistry*, 11, 1726 (1972). These represent L-amino acids, with the exception of the achiral amino acid glycine, and with the further exception of any unnatural or natural amino acids which are archiral, or are otherwise designated as D-. All peptides sequences set out herein are written according to the generally accepted convention whereby the N-terminal amino acid is on the left and the C-terminal amino acid is on the right.

Certain other abbreviations will be useful in describing this invention. The present invention employs a placement by amino acids which do not occur in nature. Particularly commonly employed among these are the following:

| Amino acid residue | Abbreviation |
|---|---|
| N,N'—guanidino-dimethyl-D-arginyl | D-Arg(Me$_2$) |
| N,N'—guanidino-diethyl-D-arginyl | D-Arg(Et$_2$) |
| N,N'—guanidiro-dibutyl-D-arginyl | D-Arg(Bu$_2$) |
| N,N'—guanidino-dimethyl-D-homoarginyl | D-hArg(Me$_2$) |
| N,N'—guanidino-diethyl-D-homoarginyl | D-hArg(Et$_2$) |
| N,N'—guanidino-dipropyl-D-homoarginyl | D-hArg(Pr$_2$) |
| N,N'—guanidino-dibutyl-D-homoarginyl | D-hArg(Bu$_2$) |
| N,N'—guanidino-methyl,butyl-D-homoarginyl | D-hArg(Me,Bu) |
| N,N'—guanidino-diisopropyl-D-homoarginyl | D-hArg(iPr$_2$) |
| N,N'—guanidino-dihexyl-D-homoarginyl | D-hArg(Hex$_2$) |
| N,N'—guanidino-dicyclohexyl-D-homoarginyl | D-hArg(dcHex$_2$) |
| N'—guanidino-ethyl-D-homoarginyl | D-hArg(Et) |
| N—guanidino-propyl-D-homoarginyl | D-hArg(Pr) |
| N—guanidino-pentyl-D-homoarginyl | D-hArg(Pe) |
| 3-(3-piperidinyl)-D-alanyl | D-3-Pia |
| 3-(4-piperidinyl)-D-alanyl | D-4-Pia |
| 3-(($N^\epsilon$—methyl)piperid-4-yl)-D-alanyl | D-Mpa |
| 3-(($N^\epsilon$—pentyl)piperid-4-yl)-D-alanyl | D-Ppa |
| 3-(($N^\epsilon$—benzyl)piperid-4-yl)-D-alanyl | D-Bpa |

Preferred compounds are:

H-Tyr-D-hArg(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-R$_{27}$-Ser-Arg-Gln-Gln-Gly-Glu-Ser-Asn-Gln-Glu-Arg-Gly-Ala-Arg-Ala-Arg-Leu-A wherein R$_{27}$ is L-Met, L-Nle or L-Leu and A is —OH or —NH$_2$;

H-Tyr-D-hArg(Me,Bu)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-R$_{27}$-Ser-Arg-Gln-Gln-Gly-Glu-Ser-Asn-Gln-Glu-Arg-Gly-Ala-Arg-Ala-Arg-Leu-A wherein R$_{27}$ is L-Met, L-Nle or L-Leu and A is —OH or —NH$_2$;

H-Tyr-D-hArg(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-R$_{27}$-Asn-Arg-Gln-Gln-Gly-Glu-Arg-Asn-Gln-Glu-Gln-Gly-Ala-Lys-Val-Arg-Leu-A wherein R$_{27}$ is L-Met, L-Nle or L-Leu and A is —OH or —NH$_2$;

H-Tyr-D-hArg(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Leu-Asn-Arg-Gln-Gln-Gly-Glu-Arg-Asn-Gln-Glu-Gln-Gly-Ala-Lys-Val-Arg-Leu-NH$_2$, (Abbrev.-[D-hArg(Et$_2$)$^2$, Leu$^{27}$]1-44-(NH$_2$)-bGRF);

H-Tyr-D-hArg(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Arg-Asn-Gln-Glu-Gln-Gly-Ala-Arg-Val-Arg-Leu-NH$_2$, (Abbrev.-[D-hArg(Et$_2$)$^2$]1-44-(NH$_2$)-pGRF);

H-His-D-hArg(Et$_2$)-Asp-Ala-Ile-Phe-Thr-Ser-Ser-Tyr-Arg-Arg-Ile-Leu-Gly-Gln-Leu-Tyr-Ala-Arg-Lys-Leu-Leu-His-Glu-Ile-Met-Asn-Arg-Gln-Gln-Gly-Glu-Arg-Asn-Gln-Glu-Gln-Arg-Ser-Arg-Phe-Asn-OH, (Abbrev.-[D-hArg(Et$_2$)$^2$]1-43(OH)-rGRF);

H-Tyr-D-hArg-(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH$_2$, ([D-hArg(Et$_2$)$^2$]1-29(NH$_2$)-hpGRF);

H-Tyr-D-Arg-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH$_2$, ([D-hArg(Et$_2$)$^2$, Nle$^{27}$]1-29(NH$_2$)-hpGRF);

H-Tyr-D-hArg(Bu$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH$_2$, ([D-hArg(Bu$_2$)$^2$, Nle$^{27}$]1-29(NH$_2$)-hpGRF);

D-hArg(Et$_2$)-Ala-Asp-Ala-Ile-Phe-Thr-Asn-Ser-Tyr-Arg-Lys-Val-Leu-Gly-Gln-Leu-Ser-Ala-Arg-Lys-

N,N'-DIALKYL SUBSTITUTED GUANIDINO AMINO ACYL RESIDUE SUBSTITUTED GRF-ANALOG PEPTIDES

This is a continuation-in-part of Ser. No. 605,346 filed Apr. 30, 1984, now abandoned, which is incorporated herein by reference.

BACKGROUND OF THE INVENTION

Physiologists have long recognized that the hypothalamus controls all the secretory functions of the adenohypophysis with the hypothalamus producing special polypeptides which trigger the secretion of each pituitary hormone. A hypothalamic releasing factor has been characterized for the pituitary hormones luteinizing hormone, follicular stimulating hormone, thyrotropin and adrenocorticotropin.

Several important hormones are produced in the mammalian hypothalamus and in the anterior lobe of the pituitary gland. One such important hormone is growth hormone which promotes mammalian growth. It has been established that release of growth hormone by the pituitary is subject to regulation by hypothalamic peptides. The concept has been well established that a substance produced in the hypothalamus, referred to as growth hormone releasing factor (GRF) or somatocrinin, promotes the release of growth hormone (GH). Somatostatin, another hypothalamic peptide, is the antagonist of somatocrinin, inhibiting the release of GH from the pituitary.

Although GRF is generally associated with the hypothalamus, it may be produced ectopically by other cells such as pancreatic tumor cells. The sequence of GRF for human pancreatic tumors has been determined (Guillemin, et al., *Science*, 218, 585-587 (1982)). It is believed that human pancreatic GRF is identical to human hypothalamic GRF [Bohlen, et al., *Biochem. and Biophys. Res. Commun.*, 144, 3, 930-936 (1983)]. Bovine, rat and porcine GRF peptides have also been isolated and sequenced, [Esch, et al., *Biochem. Biophys. Res. Commun.*, 117, 772 (1983) and references therein].

It is the purpose of this invention to provide novel GRF-analog peptides having either increased GRF activity or competitive inhibiting activity. This is accomplished by substituting for the position 1 or 2 amino residue in a GRF-analog peptide or GRF-analog peptide fragment a N,N'-dialkyl substituted argininyl or homoargininyl residue or an analog thereof or ω-nitrogen alkyl substituted lysyl analogs.

SUMMARY OF THE INVENTION

The peptides of this invention are GRF peptides or any GRF-analog fragment thereof as represented by the following formula:

$R_1$—$R_2$—$R_3$—$R_4$—Ile—Phe—Tyr—$R_8$—Ser—$R_{10}$—Arg—$R_{12}$—
—$R_{13}$—Leu—$R_{15}$—Gln—Leu—$R_{18}$—Ala—Arg—Lys—Leu—
—Leu—$R_{24}$—$R_{25}$—Ile—$R_{27}$—$R_{28}$—Arg—Gln—Gln—Gly—Glu—
—$R_{34}$—Asn—Gln—Glu—$R_{38}$—$R_{39}$—$R_{40}$—$R_{41}$—
—$R_{42}$—Thr—$R_{43}$—$R_{44}$ wherein
$R_1$ is H, D or L H-Tyr, N-MeTyr, His or $R_2$ excluding D- or L-Ala and D- or L-Leu;
$R_2$ is D- or L-Ala, D- or L-Leu or an amino acyl radical represented by the following structural formulas:
(a)

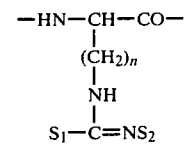

wherein
n is 1 to 5;
$S_1$ is alkyl of 1 to 12 carbon atoms, or —$NHS_3$ wherein $S_3$ is hydrogen, alkyl of 1 to 12 carbon atoms, halo lower alkyl, cycloalkyl, phenyl, benzyl, morpholino or —$(CH_2)_nN(S_4)_2$ wherein n is 1 to 5 and $S_4$ is lower alkyl;
$S_2$ is hydrogen or $S_3$, or $S_1$ and $S_2$ comprise a ring represented by the following structural formulas:

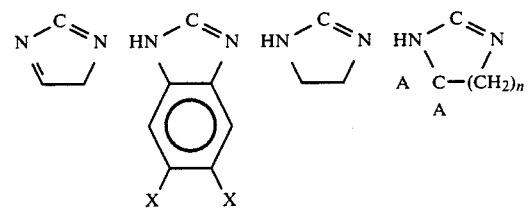

wherein n is 0, 1, 2 or 3 to 7; A is hydrogen, alkyl of 1 to 6 carbon atoms or cycloalkyl; and X is halo or A or
(b)

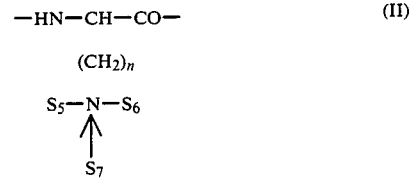

wherein $S_5$ is alkyl of 1 to 6 carbon atoms, benzyl, phenylethyl, cyclohexyl, cyclopentyl; and $S_6$ and $S_7$ are hydrogen or methyl; and n is the integer 2-5; or
(c) a substitutent of the formula

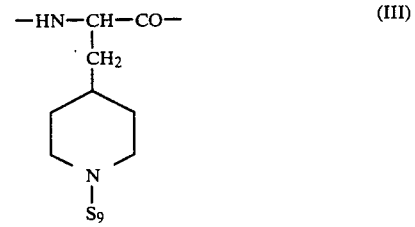

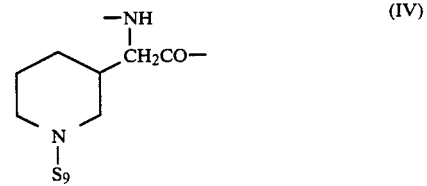

wherein
$S_9$ is hydrogen, alkyl of 1 to 12 carbon atoms, phenyl or phenyl lower alkyl; with the proviso that when $R_1$ is an amino acyl residue of formula I, II, III or IV, $R_2$ is not an amino acyl residue of formula I, II, III, or IV Leu-Leu-Gln-Asp-Ile-Nle-Ser-Arg-NH$_2$, ([D-hArg-(Et$_2$)$^1$, Nle$^{27}$]1-29(NH$_2$)-hpGRF);

H-tyr-D-hArg(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Leu-Ser-Arg-NH$_2$, ([D-hArg-(Et$_2$)$^2$, Leu$^{27}$]1-29(NH$_2$)-hpGRF);

H-Tyr-D-hArg-(CH$_2$CH$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH$_2$; and H-Tyr-D-hArg(Ch$_2$CH$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH$_2$.

H-D-hArg(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH$_2$, ([D-hArg-(Et$_2$)$^2$, Nle$^{27}$]1-29(NH$_2$)-hpGRF an antagonist).

As used herein, the term non-toxic salts refers to salts that retain the desired biological activity of the parent compound and do not impart any undesired toxicological effects. Examples of such salts are:

(a) acid addition salts formed with inorganic acids, for example, hydrochloric acid, hydrobromic acid, sulfuric acid, phosphoric acid, nitric acid and the like; and salts formed with organic acids such as, for example, acetic acid, tartaric acid, succinic acid, malic acid, citric acid, ascorbic acid, benzoic acid, and the like;

(b) salts with polyvalent metal cations such as zinc, calcium, bismuth, barium, magnesium, aluminum, copper, cobalt, nickel, cadmium, and the like; or with an organic cation formed from N,N'-dibenzylethylene-diamine or ethylenediamine; or (c) combinations of (a) and (b), e.g., a zinc tannate salt and the like.

The term "lower alkyl" refers to a straight or branched chain saturated hydrocarbon group having from 1 to 4 carbon atoms, such as, for example, methyl, ethyl, n-propyl, isopropyl, n-butyl, iso-butyl, sec-butyl and tert-butyl. "Halo lower alkyl" is a lower alkyl radical having 1, 2 or 3 halo atoms on the ω-carbon, particularly fluoro. Halo refers to fluoro, chloro and bromo. "Alkyl of 1 to 6 carbon atoms" encompasses the same substituents as lower alkyl but in addition may have 5 or 6 carbon atoms, such as, for example, a n-pentyl, n-hexyl or other branched 5 or 6 carbon member moiety. "Alkyl of 1 to 12 carbon atoms" refers to a radical of 1 to 12 carbon atoms and hydrogen only as noted above, except that the radical may have up to 12 carbon atoms. The term "cycloalkyl" refers to a cyclic saturated hydrocarbon having from 3 to 6 carbon atoms, for example, cyclopropyl, cyclobutyl, cyclopentyl and cyclohexyl.

In the practice of the method of this invention an effective amount of a compound of the invention where a pharmaceutical composition containing same is administered to the subject. These compounds or compositions may be administered by any of a variety of routes depending upon the specific end use, including orally, parenterally (including subcutaneous, intramuscular and intravenous administration, vaginally, rectally, buccally (including sublingually), transdermally or intranasally. Extended release implants based on non-degradable or degradable matrices is the preferred route of administration for these compounds.

A further aspect of the present invention relates to pharmaceutical compositions containing as analog ingredient a compound of the present invention which composition comprises such compound in admixture with a pharmaceutically acceptable, non-toxic carrier. As mentioned above, such compositions may be prepared for use for parenteral, vaginal, rectal, oral or nasal spray or aerosol form.

The compositions may conveniently be administered in unit dose form and may be prepared by any of the methods well-known in the pharmaceutical art, for example, as described in *Remington's Pharmaceutical Sciences*, Mack Publishing Company, Easton, PA 16th Ed, 1980.

It is particularly desirable to deliver the compound of this invention to the subject over prolonged periods of time, for example, for periods of one week to one year from a single administration. Various slow release, depot or implant dosage forms may be utilized. For example, a dosage form may contain a pharmaceutically acceptable non-toxic salt of the compound which has a low degree of solubility in body fluids, for example, an acid addition salt with the polybasic acid; a salt with a polyvalent metal cation; or combination of the two salts, e.g., a zinc tannate salt.

Additionally, the compounds of the present invention or, preferably, a relatively insoluble salt, may be formulated in a gel, for example, an aluminum stearate gel with, e.g., sesame oil, corn oil or the like, suitable for injection. Particularly preferred salts are zinc salts, zinc tannate salts, pamoate salts, and the like.

Another type of slow release depot formulation for injection will contain the compound or salt thereof dispersed or encapsulated in a slow degrading, non-toxic or non-antigenic polymer such as a polylactic acid/polyglycolic acid polymer, for example, as described in U.S. Pat. No. 3,773,919. The analog ingredient may also be formulated in cholesterol matrix pellets, particularly for use in animals. These compounds may also be formulated into silastic implants.

Additional slow release, depot or implant formulations are known in the literature. See, for example, *Sustained and Controlled Release Drug Delivery Systems*, J. R. Robinson, Ed., Marcel Dekker, Inc., New York, 1978.

Peptide Synthesis

Peptides of the present invention may be prepared by synthetic or recombinant DNA techniques. For example, peptides may be prepared by exclusively solid phase techniques, by partial solid phase techniques, by fragmentation condensation, by classical solution couplings, by the employment of recently developed recombinant DNA techniques, or by semi-synthesis by means of coupling fragments produced by recombinant DNA and by chemical synthesis. For example, the techniques of exclusively solid phase synthesis are set forth in the textbook *Solid Phase Peptide Synthesis*, Stuart and Young, Freeman & Co., San Francisco, 1969, and *Hormonal Proteins and Peptides*, J. Meienhofer, Vol. 2, p. 46, Academic Press (New York), 1973 for solid phase peptide syntheses and *The Peptides* by E. Schroder and K. Lubke, Vol. 1, Academic Press (New York), 1965 for classical solution syntheses.

In general, the synthetic methodologies comprise the sequential addition of one or more suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

Synthesis by recombinant DNA techniques, for the purposes of this application, include the suitable employment of a structural gene coding for the desired GRF-analog peptide. The synthetic peptide may be obtained by transforming a microorganism using an expression vector including a promoter and operator together with such structural gene and causing such transformed microorganism to express the GRF-analog peptide. A non-human animal may also be used to produce the GRF-analog peptide by gene-farming using such a structural gene and the general techniques set forth in U.S. Pat. No. 4,276,282 issued June 30, 1981 or using micro injection of embryos as described in WO 83/01783 published May 26, 1983 and WO 82/04443 published Dec. 23, 1982. The GRF-analog peptide may also be produced directly in the animal for which accelerated growth is intended by the techniques described in the two WO publications.

Preferred Synthetic Embodiments

A particularly preferred method of preparing compounds of the present invention involves solid phase peptide synthesis.

In this particularly preferred method the $N^\alpha$-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, $N^\alpha,N^\alpha$-dimethyl-3,5-dimethoxybenzyloxycarbonyl, o-nitrophenylsulfenyl, 2-cyano-t-butyloxycarbonyl, 9-fluorenylmethyloxycarbonyl and the like, especially t-butyloxycarbonyl (Boc).

Particularly preferred side chain protecting groups are, for arginine:nitro, p-toluenesulfonyl, 4-methoxybenzenesulfonyl, Cbz, Boc and adamantyloxycarbonyl; for tyrosine:benzyl, o-bromobenzyloxycarbonyl, 2,6-dichlorobenzyl, isopropyl, cyclohexyl, cyclopentyl and acetyl; for serine and threonine:benzyl, acetyl and tetrahydropyranyl; for histidine: benzyl, p-toluenesulfonyl and 2,4-dinitrophenyl; for aspartic acid and glutamic acid:benzyl, cyclohexyl; lysine: O-chlorobenzyloxycarbonyl or Cbz.

The C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer, and the like, especially chloromethyl-polystyrene-1% divinylbenzene polymer. For the special case where the C-terminus of the compound will be an amide, a particularly useful support is the benzhydrylamino-polystyrene-divinylbenzene polymer described by P. Rivaille, et al, Helv. Chim. Acta., 54, 2772 (1971) or the p-methylbenzylamino-poylstyrene-divinylbenzene polymer described by Stewart, et al., Peptides, 2, 45 (1981). The attachment to the chloromethyl polystyrene-divinylbenzene type of resin is made by means of the reaction of the $N^\alpha$-protected amino acid, especially the Boc-amino acid, as its cesium, tetramethylammonium, triethylammonium, 1,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between about 40 and 60° C, preferably about 50° C., for from about 12 to 48 hours, preferably about 24 hours. The $N^\alpha$-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10 and 50° C., preferably 25° C. in a solvent such as dichloromethane or DMF, preferably dichloromethane. The coupling of successive protected amino acids can be carried out in an automatic polypeptide synthesizer as is well known in the art. The removal of the $N^\alpha$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane, dichloromethane/DMF mixtures, DMF and the like, especially in dichloromethane/DMF, at about ambient temperature. The coupling agent is normally DCC in dichloromethane but may be N,N'-di-iso-propylcarbodiimide (DIC) or other carbodiimide either alone or in the presence of HBT, N-hydroxysuccinimide, other N-hydroxyimides or oximes. Alternately, protected amino acid analog esters (e.g. p-nitrophenyl, pentafluorophenyl and the like) or symmetrical anhydrides may be used.

At the end of the solid phase synthesis the fully protected polypeptide is removed from the resin. When the linkage to the resin support is of the benzyl ester type, cleavage is by means of aminolysis with an alkylamine or fluoroalkylamine for peptides with a alkylamide C-terminus, or by aminolysis with, for example, ammonia/methanol or ammonia/DMF for peptides with an amide C-terminus at a temperature between about 10° and 50° C., preferably about 25° C., for between about 12 and 24 hours preferably about 18 hours. Alternatively, the peptide may be removed from the resin by transesterification, e.g., with methanol, followed by aminolysis. The protected peptide may be purified at this point by silica gel chromatography. The removal of the side chain protecting groups from the polypeptide is performed by treating the aminolysis product with, for example, anhydrous liquid hydrogen fluoride in the presence of anisole or other carbonium scavenger, treatment with hydrogen fluoride/pyridine complex, treatment with tris(trifluoroacetyl)boron and trifluoroacetic acid, by reduction with hydrogen and palladium on carbon or on polyvinylpyrrolidone, or by reduction with sodium in liquid ammonia, preferably with liquid hydrogen fluoride, and anisole at a temperature between about $-10°$ and $+10°$ C., preferably about $0°$ C., for between about 15 minutes and 2 hour, preferably about 1 hour. For the peptides on the benzyhydrylamine resins, the resin cleavage and deprotection steps may be combined in a single step utilizing liquid hydrogen fluoride and anisole as described above. The fully deprotected polypeptide is then purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g., on Sephadex G-25, or countercurrent distribution; high performance liquid chromatography (HPLC), especially reverse phase HPLC on octyl- or octadecylsilyl-silica bonded phase column packing.

Thus, in another aspect the present invention relates to a method for preparing compounds of the invention and of the pharmaceutically acceptable salts thereof which process comprises:
(i) removing a protecting group and optionally covalently bound solid support from a protected polypeptide to afford a compound of formula (I) or a salt thereof; or
(ii) converting a compound of Formula (I) to a pharmaceutically acceptable salt;
(iii) converting a salt of a compound of Formula (I) to a different pharmaceutically acceptable salt, or
(iv) converting a salt of a compound of Formula (I) to a free polypeptide of Formula (I).

Alternatively, the compounds of this invention may be prepared by:
coupling in the required sequence an amino acid or peptide fragment with a second peptide fragment of the compound of Formula (I) or a salt thereof;
(ii) converting a compound of Formula (I) to a pharmaceutically acceptable salt;
(iii) converting a salt of a compound of Formula (I) to a different pharmaceutically acceptable salt; or
(iv) converting a salt of a compound of Formula (I) to a free polypeptide of Formula (I).

The following examples are given to enable those skilled in the art to more fully understand and practice the present invention. They should not be construed as a limitation upon the scope of the invention, but merely as being illustrative and representative thereof.

PREPARATION 1

A mixture of 5.24 g of benzyl $N^\alpha$-benzyloxycarbonyl-D-lysinate toluenesulfonate (B. Bezas and L. Zervas, J. Am. Chem. Soc. 83, 719 (1961) and 1.72 ml of diisopropylethylamine in 60 ml of dioxane is treated with 1.89 g of N,N'-diisopropylcarbodiimide. The reaction mixture is stirred at 100° C. for 6 hours, cooled to room temperature and concentrated to a solid. The solid is suspended in 20 ml of warm DMF, filtered to remove N,N'-diisopropylurea and the filtrate concentrated to a solid. Benzyl $N^\alpha$-benzyloxycarbonyl-N,N'-guanidino-diisopropyl-D-homoargininate toluenesulfonate is obtained as a white solid by crystallization from methanol/ethyl acetate $[\alpha]_D^{25}$ 4.71° (C 1, MeOH).

Similarly, by using the above procedure, but substituting:
N,N'-dimethylcarbodiimide;
N,N'-diethylcarbodiimide;
N,N'-di-n-propylcarbodiimide;
N,N'-di-i-propylcarbodiimide;
N,N'-di-n-butylcarbodiimide;
N,N'-di-i-butylcarbodiimide;
N,N'-di-n-pentylcarbodiimide;
N,N'-di-i-pentylcarbodiimide;
N,N'-dicyclohexylcarbodiimide;
N,N'-di-n-hexylcarbodiimide;
N,N'-diphenylcarbodiimide;
N,N'-ditolylcarbodiimide; or
N-i-propylcarbodiimide;
N-propylcarbodiimide;
N,N'-bis(2,2,2-trifluoroethyl)carbodiimide;
1-(3-dimethylaminopropyl)-3-ethylcarbodiimide-HCl
and the like, there are obtained:
benzyl $N^\alpha$-benzyloxycarbonyl-N,N'-guanidinodimethyl-D-homoargininate;
benzyl $N^\alpha$-benzyloxycarbonyl-N,N'-guanidinodiethyl-D-homoargininate, $[\alpha]_D^{25}$ 12.9° (C 0.1, MeOH);
benzyl $N^\alpha$-benzyloxycarbonyl-N,N'-guanido-di-n-propyl-D-hommoargininate $[\alpha]_D^{25}$ 10.9° (C 0.9, MeOH);
benzyl $N^\alpha$-benzyloxycarbonyl-N,N'-guanidino-di-n-propyl-D-homoargininate $[\alpha]_D^{25}$ 14.7° (C 0.4 MeOH);
benzyl $N^\alpha$-benzyloxycarbonyl-N,N'-guanidino-di-n-butyl-D-homoargininate $[\alpha]_D^{25}$ 10.7° (C 0.6, MeOH);
benzyl $N^\alpha$-benzyloxycarbonyl-N,N'-guanidino-di-n-pentyl-D-homoargininate;
benzyl $N^\alpha$-benzyloxycarbonyl-N,N'-guanidino-di-i-pentyl-D-homoargininate;
benzyl $N^\alpha$-benzyloxycarbonyl-N,N'-guanidino-dicyclohexyl-D-homoargininate, $[\alpha]_D^{25}$ 8.07° (C 0.9 MeOH);
benzyl $N^\alpha$-benzyloxycarbonyl-N,N'-guanidino-di-n-hexyl-D-homoargininate, $[\alpha_D^{25}$ 10.1° (C 0.4, MeOH)
benzyl $N^\alpha$-benzyloxycarbonyl-N,N'-guanidino-di-phenyl-D-homoargininate, $[\alpha]_D^{25}$ 4.25° (C 0.4, MeOH)
benzyl $N^\alpha$-benzyloxycarbonyl-N,N'-guanidino-bis(2,2,2-trifluoroethyl)-D-homoargininate; and
benzyl $N^\alpha$-benzyloxycarbonyl, N-guanidino-(3-dimethylaminopropyl)-N'-guanidino-ethyl-D-homoargininate $[\alpha]_D^{25}$ 11.7° (C 0.1, MeOH) as their toluenesulfonate salts.

Similiarly, by substituting benzyl N$\alpha$-benzyloxycarbonyl-D-ornithinate for the D-lysinate there may be obtained the corresponding arginine analogs as their toluenesulfonate salts, for example,
benzyl $N^\alpha$-benzyloxycarbonyl-N,N'-guanidino-di-isopropyl-D-argininate, $[\alpha]_D^{25} -10.5°$ (C 0.5, MeOH).

PREPARATION 2

Benzyl $N^\alpha$-benzyloxycarbonyl-$N^G$, $N^{G'}$-ethano-D-homoargininate

To a mixture of 15 ml of toluene and 15 ml of t-BuOH was added 2.71 g of benzyl $N^\alpha$-benzyloxycarbonyl-D-lysinate and 1.46 g of 2-methylthioimidazoline .HI (available from Aldrich). The pH of the mixture was brought to ~8 by the addition of diisopropylethylamine and the solution heated under reflux for 24 hours.

The solution was concentrated in vacuo and the residue was loaded on a silica gel column (250 g). The column was eluted with a gradient from $CH_2Cl_2$/MeOH (19:1) to $CH_2Cl_2$/MeoH (7:3). The fractions containing product were detected by TLC, pooled, and concentrated to dryness, 2.9 g of white foam.

A 2 g portion of the above-named product was dissolved in 50 ml of EtOH containing 0.8 g of 10% Pd/C. The solution was stirred under $H_2$ for 8 hours. The mixture was filtered on celite and the filtrate was concentrated to dryness to give $N_G$, $N^G$-etheno-D-homoarginine as a white foam, 1.2 g.

(ii) $N^\alpha$-Boc-$N^G$,$N^{G'}$-ethano-D-homoarginine

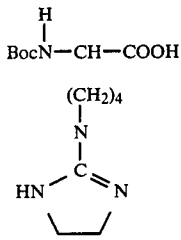

A solution of 2.74 g of D-lysine dihydrochloride and 4.03 g of 2-methylthio-2-imidazoline.hydroiodide in 16.5 ml of 2N NaOH was stirred at room temperature for 6 days. Analysis of the reaction mixture on an amino acid analyzer showed that ~70% of the desired ε-dialkylguanido compound had been formed. A further 0.25 g of the 2-methylthio-2-imidazoline.hydroiodide and 1 ml of 2N NaOH were added and the reaction was continued at room temperature for 3 more days.

The reaction mixture was treated with 0.8 g MgO and 4.36 g of di-tert-butyldicarbonate in 20 ml of dioxane. The pH was adjusted to 9.5 with 1N NaOH. After overnight reaction some starting material was present, so 1 g of di-tert-butyldicarbonate was added.

The mixture was filtered and the filtrate was concentrated to dryness. The residue was dissolved in $H_2O$ and washed with $Et_2O$ and the aqueous layer was adjusted to pH 4 with HOAc. The acidic solution was washed with EtOAc. The aqueous layer containing the product was treated with anion exchange resin (AG-3 acetate, Bio-Rad) and concentrated to dryness.

The crude product was passed through a hydrophobic chromatography column (Amberlite XAD-2, Rohm & Haas) by elution with a gradient from $H_2O$ to 25% EtOH. The fractions containing product were pooled to yield 2.7 g of $N^\alpha$-Boc-$N^G$,$N^{G'}$-ethano-D-homoarginine as its acetate salt, $[\alpha]_D^{25}-19.7°$ (C 0.1, MeOH).

In a similar fashion, by substituting:
S-methyl-dimethyl-iso-thiourea-HI,
S-methyl-diethyl-iso-thiourea-HI,
S-methyl-dipropyl-iso-thiourea-HI,
S-methyl-dibutyl-iso-thiourea-HI,
S-methyl-dipentyl-iso-thiourea-HI,
S-methyl-dihexyl-iso-thiourea-HI,
S-methyl-diheptyl-iso-thiourea-HI,
S-methyl-dinonyl-iso-thiourea-HI,
S-methyl-diphenyl-iso-thiourea-HI,
S-methyl,N-methyl,N'-ethyl-iso-thiourea-HI,
S-methyl,N-methyl,N'-propyl-iso-thiourea-HI,
S-methyl,N-methyl,N'-butyl-iso-thiourea-HI, and
S-methyl,N-methyl,N'-hexyl-iso-thiourea-HI
for 2-methylthio-2-imidazoline-HI, there are obtained:
S-methyl-dimethyl-iso-thiourea-HI, $[\alpha]_D^{25}-19.5°$ (C 0.1, MeOH);
$N^\alpha$-Boc-N,N'-guanidino-diethyl-D-homoarginine, $[\alpha]_D^{25}$, $-19.7°$ (C 0.1, MeOH);
$N^\alpha$-Boc-N,N'-guanidino-dipropyl-D-homoarginine, $[\alpha]_D^{25}$, $-11.3°$ (C 0.5, MeOH);
$N^\alpha$-Boc-N,N'-guanidino-dibutyl-D-homoarginine, $[\alpha]_D^{25}$ $-6.3°$ (C 0.5, MeOH)
$N^\alpha$-Boc-N-N'-guanidino-dipentyl-D-homoarginine,
$N^\alpha$-Boc-N,N'-guanidino-dihexyl-D-homoarginine, $[\alpha]_D^{25}$,
$N^\alpha$-Boc-N,N'-guanidino-diheptyl-D-homoarginine,
$N^\alpha$-Boc-N,N'-guanidino-dinonyl-D-homoarginine,
$N^\alpha$-Boc-N,N'-guanidino-diphenyl-D-homoarginine, $[\alpha]_D^{25}$, $-9.2°$ (C 0.8, MeOH);
$N^\alpha$-Boc-N,N'-guanidino-methyl,ethyl-D-homoarginine,
$N^\alpha$-Boc-N,N'-guanidino-methyl,propyl-D-homoarginine, and
$N^\alpha$-Boc-N,N'-guanidino-methyl,butyl-D-homoarginine,
$N^\alpha$-Boc-N,N'-guanidino-methyl,hexyl-D-homoarginine, $[\alpha]_D^{25}-2.2$ (C 0.4, EtOH).

PREPARATION 3

This Preparation illustrates the preparation of $N^\alpha$-t-butyloxy carbonyl derivatives of N,N'-guanidino-disubstituted-D-homoarginines from their toluenesulfonate precursors.

A mixture of benzyl $N^\alpha$-benzyloxycarbonyl-N,N'-guanidino-diisopropyl-D-homoargininate toluenesulfonate (3.25 g) and 100 mg of 10% Pd/C in 50 ml of glacial acetic acid is treated with hydrogen gas at atmospheric pressure for 4 hours. The catalyst is filtered on celite and the filtrate is concentrated to a solid, N,N'-guanidino-diisopropyl-D-homoarginine toluenesulfonate. A solution of this compound (2.13 g) in 60 ml of 50% dioxane/water is treated with 10 ml of 1N sodium hydroxide and 0.4 g of magnesium oxide. This mixture is then treated with 1.1 g of di-t-butyldicarbonate and stirred at room temperature for 2 hours. The magnesium salt is filtered and the filtrate is concentrated under vacuum. The basic solution is washed with ether, then brought to pH 2.5 with sodium sulfate. The acidic aqueous solution is extracted with ethylacetate which is dried over magnesium sulfate. The drying agent is filtered and the filtrate is conentrated. Evaporation of the solvent affords $N^\alpha$-t-butyloxycarbonyl-N,N'-guanidino-diisopropyl-D-homoarginine toluenesulfonate, $[\alpha]_D^{25}$ $-1.2°$ (C 0.7, MeOH).

Proceeding in a similar manner, but substituting the appropriate toluenesulfonate precursors, other $N^\alpha$-t-butyloxycarbonyl-N,N'-guanidino-disubstituted-D-homoarginine or D-arginine compounds may be prepared.

PREPARATION 4

Nα-t-butyloxycarbonyl-3-(1'-propylpiperid-4-yl)-D-alanine

A 4.6 g portion of sodium metal was added to 400 ml of absolute ethanol and heated. To the resultant solution of sodium ethoxide was added 21.7 g of diethyl acetamidomalonate and 16.4 g of 4-picolyl chloride hydrochloride (Aldrich Chem. Co.). The reaction mixture was heated to 100° C. for 4 hours, cooled, filtered and concentrated in vacuo. The mixture was loaded on a silica gel column in methylene chloride/methanol (19:1) and eluted with the same mixture. The product was located as a fast running UV position spot by TLC on silica gel in methylene chloride/methanol (19:1).

Combined fractions were concentrated to provide the product.

The product from the foregoing paragraph was dissolved in 200 ml of ethanol and treated with a solution of 2.72 g of sodium hydroxide in 40 ml of water at 50° C. for 6 hours. The solution was acidified with 12 ml of 6N HCl, concentrated to dryness and taken up in 200 ml of dioxane. The suspension was filtered and the filtrate heated at reflux for 2 hours. The solution was cooled and concentrated to dryness to yield ethyl $N^{\alpha}$-acetyl-3-(4-pyridyl)-D,L-alaninate as a white solid, m.p. 120°-122° C.

A portion of this N-acetyl ester was resolved by treatment with 200 mg of the enzyme subtilisin Carlsberg (Sigma Chem. Co., protease VIII) in a mixture of 300 ml of dimethyl sulfoxide and 400 ml of 0.01M KCl (pH 7.2). The pH was maintained by addition of 1N NaOH on a pH Stat. After a 6 hour period, the resolution was complete. The solution was diluted with 400 ml of water and extracted with 4×750 ml of ethyl acetate. The organic layers were combined and dried over magnesium sulfate and concentrated to yield ethyl $N^{\alpha}$-acetyl-3-(4-pyridyl)-D-alaninate as an oil, $[\alpha]_D^{25} -1.61°$ (C 1, MeOH).

The oil was reacted with 1.22 g of n-propyl bromide in 50 ml of ethanol after which the solution was concentrated to dryness to yield ethyl $N^{\alpha}$-acetyl-3-(1-propylpyridinium-4-yl)-D-alininate bromide as a white hygroscopic solid.

This white solid was dissolved in 200 ml of ethanol and was reduced under an atmosphere of hydrogen gas using 100 mg of 10% Pd/C as a catalyst. After an 18 hour reduction period, the catalyst was filtered off and the solution concentrated to yield ethyl $N^{\alpha}$-acetyl-3-(1-propylpiperidin-4-yl)-D-alininate as a tan solid. The free acid was prepared by refluxing the ethyl ester in 100 ml of 6N HCl for 4 hours to yield 3-(1-propylpiperidin-4-yl)-D-alanine as a white solid.

The free acid was dissolved in 100 ml of dioxane/water (1:1) and treated with 2 g of di-t-butyldicarbonate. The pH was maintained at 9 by addition of 1N NaOH on a pH Stat. After 2 hours the reaction mixture was concentrated in vacuo, washed with 100 ml of ethyl ether and the aqueous layer was loaded on an Amberlite XAD-2 hydrophobic resin. The column was eluted with 250 ml of water followed by 250 ml of 50% ethanol/water. The ethanol eluate was pooled and concentrated to dryness to yield $N^{\alpha}$-t-butyloxycarbonyl-3-(1-propylpiperidin-4-yl)-D-alanine as a white solid.

Proceeding in similar manner, but substituting 3-picolyl chloride hydrochloride for 4-picolyl chloride hydrochloride, there is prepared $N^{\alpha}$-t-butyloxycarbonyl-3-(1-propylpiperidin-4-yl)-D-alanine.

EXAMPLE 1

Preparation of [D-hArg(Et$_2$)$^2$]1-29(NH$_2$)-hGRF

The reaction vessel of a Beckman 990 Synthesizer was loaded with 3.5 g (3 mmol available NH$_2$) of benzhydrylaminopolystyrene-1%-divinylbenzene resin (Beckman, Inc.). The resin was washed twice with 10% triethylamine/methylene chloride, three times with methylene chloride and then was allowed to react with 3.2 g Boc-Arg(Tos)-OH and 1.02 g of HBT for ca. 3 hours at room temperature. The initial coupling was shown to be complete by the Kaiser test. Further couplings were carried out using the program described above using from 1.6 to 2.5 (usually 2.5) equivalents of protected amino acid:

| | |
|---|---|
| 2.21 g | Boc—Ser(Bzl)—OH |
| 1.87 g | Boc—Met—OH |
| 1.80 g | Boc—Ile—OH.½H$_2$O |
| 2.4 g | Boc—Asp(OBzl)—OH |
| 1.4 g | Boc—Gln—OH and 0.8 g HBT |
| 1.87 g | Boc—Leu—OH.H$_2$O |
| 1.87 g | Boc—Leu—OH.H$_2$O |
| 3.3 g | Boc—Lys(Cl—Z)—OH.t-But—NH$_2$ salt in free acid form |
| 3.2 g | Boc—Arg(Tos)—OH |
| 1.42 g | Boc—Ala—OH |
| 2.21 g | Boc—Ser(Bzl)—OH |
| 1.87 g | Boc—Leu—OH.H$_2$O |
| 1.4 g | Boc—Gln—OH and 0.8 g HBT |
| 1.31 g | Boc—Gly—OH |
| 1.87 g | Boc—Leu—OH.H$_2$O |
| 1.62 g | Boc—Val—OH |
| 3.3 g | Boc—Lys(Cl—Z)—OH.t-ButNH$_2$ as the free acid form |
| 3.2 g | Boc—Arg(Tos)—OH |
| 3.3 g | Boc—Arg(Cl$_2$—Bzl)—OH |
| 2.21 g | Boc—Ser(Bzl)—OH |
| 1.4 g | Boc—Asn—OH and 0.8 g HBT |
| 2.32 g | Boc—Thr(Bzl)—OH |
| 1.99 g | Boc—Phe—OH |
| 1.80 g | Boc—Ile—OH.½H$_2$O |
| 1.42 g | Boc—Ala—OH and |
| 2.4 g | Boc—Asp(OBzl)—OH. |

At this point the peptide resin weighed 11.2 g and was split into portions for the preparation of several analogs.

A 1.7 g portion of the 27 residue peptide resin was placed in the synthesizer and further deprotected and reacted as above with:

| | |
|---|---|
| 0.34 g | Boc—D-hArg(Et$_2$)—OH and |
| 0.66 g | Boc—Tyr(Cl$_2$—Bzl)—OH. |

This resulted in 1.8 g of protected peptide resin.

A 0.9 g portion of this peptide resin was deprotected and cleaved from the resin by treatment at 0° C. for 1 hour with 10 ml of anhydrous (CoF$_3$), redistilled liquid HF in the presence of 0.9 ml of anisole as scavanger. The HF was removed in vacuo and the residue was washed with 3×10 ml of 50% aqueous acetic acid and passed through a weakly basic AG-3 column (Bio-Rad) in the acetate form to remove fluoride ions.

The crude product was purified in 2 portions of 210 mg by reversed-phase preparative HPLC on a 2.2×50 cm Partisil 10 ODS-3, m 20-50 (10μm) column (Whatman). The eluent was 33% acetonitrile/67% H$_2$O containing 0.1% trifluoroacetic acid. Elution was at 11.2 ml/min. The product peaks were analyzed by HPLC on a 0.4×25 cm, 5 μm C-18 column (Vydac, Separation Sciences) and were pooled for purity rather than yield. Two pools of the ([D-hArg(Et$_2$)$^2$]1-29(NH$_2$) hGRF product were obtained which totaled 67 mg; mp—120°-130° (dec); [α] −35.7 (C$^{0.4}$, H$_2$O) and which gave the correct amino acid analysis. Alternatively, sequential gel permeation chromatography on Sephadex G-50 in 0.2M acetic acid followed by ion exchange chromatography on carboxymethylcellulose (gradient from 0.01M ammonium acetate, pH 4.5 to 1M ammonium acetate pH 6.5) gave a product of similar purity.

Proceeding in a similar fashion, but substituting the appropriate protected amino acid for those described above, there was obtained:

[D-hArg(CH$_2$CH$_2$)]1-29(NH$_2$-hGRF, mp—152°-155° C. and [α]$_D^{25}$ −31.0°0 (C 0.2, H$_2$O);
[D-hArg(Et$_2$)$^2$, Nle$^{27}$]1-29(NH$_2$)-hGRF, m.p. 167°(dec) and [α]$_D^{25}$ −37.6°(C 0.4, H$_2$O);
[D-Arg$^2$, Nle$^{27}$]1-29(NH$_2$)-hpGRF, m.p. 174°(dec) and [α]$_D^{25}$ −36.0°(C 0.6, H$_2$O);
[D-hArg(Et$_2$)$^2$]1-15(NH$_2$)-hGRF, mp—180°-190° C., [α]$_D^{25}$ −34.4°(C 0.4, H$_2$O);
[N-Me-Tyr$^1$, D-hArg(Et$_2$)$^2$]1-15(NH$_2$)-hGRF, mp—170°-180° C., [α]$_D^{25}$ −33.2° (C 0.3, H$_2$O);
[D-hArg(Et$_2$)$^2$, Gly$^{15}$-NHEt]1-15-hGRF, mp 170°-180° C., [α]$_D^{25}$ −18.6° (C 0.2, H$_2$O);
[D-hArg(CH$_2$CH$_2$)$^2$, Nle$^{27}$]1-29(NH$_2$)-hGRF, m.p. 164° (dec), [α]$_D^{25}$ −44.1° (C 0.5, H$_2$O);
[N-Me-Tyr$^1$, D-hArg(Et$_2$)$^2$, Nle$^{27}$]1-29-(NH$_2$)-hGRF, m.p. 164° (dec), [α]$_D^{25}$ −38.2° (C 0.3, H$_2$O);
[D-hArg(Et$_2$)$^2$, Leu$^{27}$]1-44(NH$_2$)hpGRF;
[D-hArg(Et$_2$)$^2$, Leu$^{27}$]1-44(OH)hpGRF;
[D-hArg(Pr$_2$)$^2$, Leu$^{27}$]1-44(NH$_2$)hpGRF;
[D-hArg(Bu$_2$)$^2$, Leu$^{27}$]1-44(NH$_2$)hpGRF;
[N-Me-Tyr$^1$,D-hArg(Et$_2$)$^2$,Leu$^{27}$]1-44(NH$_2$)-hpGRF;
[D-hArg(Me,Bu)$^2$,Leu$^{27}$]1-44(NH$_2$)hpGRF;
[D-hArg(Me,Bu)$^2$,Leu$^{27}$]1-44(OH)hpGRF;
[D-hArg(Me,hexyl)$^2$,Leu$^{27}$]1-44(NH$_2$)hpGRF;
[D-hArg(Me,Bu)$^2$,Nle$^{27}$]1-44(NH$_2$)hpGRF;
[D-hArg(Et$_2$)$^1$,Nle$^{27}$]1-44(NH$_2$)hpGRF;
[D-hArg(Et$_2$)$^1$,Nle$^{27}$]1-44(OH)hpGRF;
[D-hArg(Bu$_2$)$^2$,Nle$^{27}$]1-29(NH$_2$)hpGRF;
[D-hArg(Pr$_2$)$^2$,Nle$^{27}$]1-29(NH$_2$)hpGRF;
[D-hArg(Et$_2$)$^1$,Nle$^{27}$]1-29(NH$_2$)hpGRF;
[D-hArg(Et$_2$)$^2$,Nle$^{27}$]1-29(NH$_2$)hpGRF;
[D-hArg(Me,Bu)$^2$,Nle$^{27}$]1-29(NH$_2$)hpGRF; and
[D-hArg(Me,Hexyl)$^2$,Nle$^{27}$]1-29(NH$_2$)hpGRF.

In a similar manner, deletion of the N-Terminal Tyr residue yields antagonistic analogs of GRF, for example:
[D-hArg(Et$_2$)$^2$,Nle$^{27}$]2-29(NH$_2$)hpGRF
[D-hArg(Et$_2$)$^2$, Leu$^{27}$]2-29(NH$_2$)hpGRF
[D-hArg(Et)$^2$,Nle$^{27}$]2-29(NH$_2$)hpGFR
[D-hArg(Me,Bu)$^2$,Nle$^{27}$]2-29(NH$_2$)hpGFR and the like

EXAMPLE 2

Long Acting intramuscular injectable formulation.

| 1. Long Acting I.M. Injectable - Sesame Oil Gel | |
|---|---|
| GRF-Active Peptide | 10.0 mg |
| Aluminum monostearate, USP | 20.0 mg |
| Sesame oil q.s. ad | 1.0 ml |

The aluminum monostearate is combined with the sesame oil and heated to 125° C. with stirring until a clear yellow solution forms. This mixture is then autoclaved for sterility and allowed to cool. The GRF-analog peptide is then added aseptically with trituration. Particularly preferred GRF-analog peptides are salts of low solubility, e.g. zinc salts, zinc tannate salts, pamoate salts, and the like. These exhibit exceptionally long duration of activity.

| 2. Long Acting I.M. Injectable - Biodegradable Polymer | |
|---|---|
| GRF-Active Peptide | 1% |
| 25/75 glycolide/lactide copolymer (0.5 intrinsic viscosity) | 99% |

Microcapsules of above formulation suspended in:

| | |
|---|---|
| Dextrose | 5.0% |
| CMC, sodium | 0.5% |
| Benzyl alcohol | 0.9% |
| Tween 80 | 0.1% |
| Water, purified q.s. | 100.0% |

25 mg of microcapsules would be suspended in 1.0 ml of vehicle.

| C. Aqueous Solution for Intramuscular Injection | |
|---|---|
| GRF-Active Peptide | 500 mg |
| Gelatin, nonantigenic | 5 mg |
| Water for injection q.s. ad | 100 ml |

Dissolve gelatin and GRF-analog peptide in water for injection, then sterile filter solution.

What is claimed is:

1. A GRF-analog peptide of the formula

R$_1$—R$_2$—R$_3$—R$_4$—Ile—Phe—Tyr—R$_8$—Ser—R$_{10}$—Arg—R$_{12}$—
—R$_{13}$—Leu—R$_{15}$—Gln—Leu—R$_{18}$—Ala—Arg—Lys—Leu—
—Leu—R$_{24}$—R$_{25}$—Ile—R$_{27}$—R$_{28}$—Arg—Gln—Gln—Gly—Glu—
—R$_{34}$—Asn—Gln—Glu—R$_{38}$—R$_{39}$—R$_{40}$—R$_{41}$—
—R$_{42}$—Thr—R$_{43}$—R$_{44}$ and the pharmaceutically non-toxic salts thereof wherein R$_1$ is H, D or L H-Tyr, N-MeTyr, His or R$_2$ excluding D- or L-Ala and D- or L-Leu;

R$_2$ is D- or L-Ala, D- or L-Leu or an amino acyl radical represented by the following structural formulas:

(a)

$$-HN-CH-CO- \quad (I)$$
$$| $$
$$(CH_2)_n$$
$$|$$
$$NH$$
$$|$$
$$S_1-C=NS_2$$

wherein n is 1 to 5;

S$_1$ is alkyl of 1 to 12 carbon atoms, or —NHS$_3$ wherein S$_3$ is hydrogen, alkyl of 1 to 12 carbon atoms, halo lower alkyl, cycloalkyl, phenyl, benzyl, morpholino or —(CH$_2$)$_n$N(S$_4$)$_2$ wherein n is 1 to 5 and S$_4$ is lower alkyl;

S$_2$ is hydrogen, or S$_3$ or S$_1$ and S$_2$ comprise a ring represented by the following structural formulas:

wherein m is 1 to 7; A is hydrogen, alkyl of 1 to 6 carbon atoms or cycloalkyl; ad X is halo or A or (b) a substituent of the formula

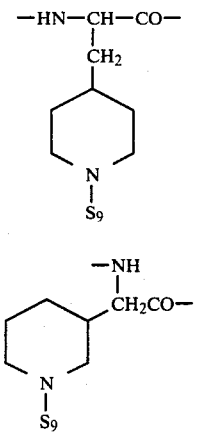

wherein $S_9$ is hydrogen, alkyl of 1 to 12 carbon atoms, phenyl or phenyl lower alkyl; with the proviso that when $R_1$ is an amino acyl residue of formula I, III or IV, $R_2$ is not an amino acyl residue of formula I, III or IV, and when $R_1$ is D or L Tyr, N MeTyr or His, $R_2$ may not be D or L Ala or Leu; $R_3$ is Asp, Asn or Glu; $R_4$ is Ala or Gly; $R_8$ is Asn or Ser; $R_{10}$ is Tyr, D-Tyr or Phe; $R_{12}$ is Lys or Arg; $R_{13}$ is Ile or Val; $R_{15}$ is Gly or D-Ala; $R_{18}$ is Ser or Tyr; $R_{24}$ is Gln or His; $R_{25}$ is Glu or Asp; $R_{27}$ is D,L-Ala, D,L-Nle, D,L-Ile, D,L-Leu, D,L-Met, D,L-Val; $R_{28}$ is Asn, Ser or D-Ala; $R_{34}$ is Arg, Ser or Ala; $R_{38}$ is Gln, Arg or Ser; $R_{39}$ is Arg or Gly; $R_{40}$ is Ala, Ser, Arg or Des-$R_{40}$; $R_{41}$ is Arg, Phe, Lys or Des-$R_{41}$; $R_{42}$ is Val, Phe, Ala, Gln, Gly, Ile, Leu, Lys, Pro or Des-$R_{42}$; and $R_{43}$ is Asn, Arg or des-$R_{43}$; $R_{44}$ is Leu, or Des-$R_{44}$; and GRF-analog fragments thereof which at contain least so many amino acids as to include $R_{28}$-Arg and the N-terminal fragment $R_1$-$R_2$-$R_3$-$R_4$- as defined herein.

2. A compound according to claim 1 wherein $R_2$ is an amino acyl radical represented by the following structural formulas:

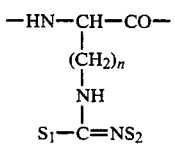

wherein
n is 1 to 5;
$S_1$ is alkyl of 1 to 12 carbon atoms, —$NHS_3$ wherein $S_3$ is hydrogen, alkyl of 1 to 12 carbon atoms, halo lower alkyl, cycloalkyl, phenyl, benzyl, morpholino or —$(CH_2)_nN(S_4)_2$ wherein n is 1 to 5 and $S_4$ is lower alkyl; and
$S_2$ is hydrogen, alkyl of 1 to 12 carbon atoms, cycloalkyl, phenyl, benzyl or halo lower alkyl.

3. A compound according to claim 2 wherein $R_2$ is a radical of formula I wherein $S_1$ is —$NHS_3$ wherein $S_3$ is alkyl of 1 to 12 carbon atoms, halo lower alkyl or phenyl and $S_2$ is independently alkyl of 1 to 12 carbon atoms, halo lower alkyl or phenyl, and $R_{27}$ is L-Nle or L-Leu.

4. A compound of claim 1 where $R_1$=H, which is an antagonist of GRF.

5. A compound of claim 4 which is [D-hArg(Et$_2$)$^2$,-Nle$^{27}$]2-29(NH$_2$)hpGRF, a GRF antagonist.

6. A compound of claim 4 which is [D-hArg(Et$_2$)$^2$,Leu$^{27}$]2-29(NH$_2$)hpGRF, a GRF antagonist.

7. A compound according to claim 3 which is H-Tyr-D-hArg(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-$R_{27}$-Ser-Arg-Gln-Gln-Gly-Glu-Ser-Asn-Gln-Glu-Arg-Gly-Ala-Arg-Ala-Arg-Leu-A wherein $R_{27}$ is L-Met, L-Nle or L-Leu and A is —OH or —NH$_2$ and the pharmaceutically acceptable non-toxic salts thereof.

8. A compound according to claim 3 which is H-Tyr-D-hArg(Me,Bu)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-$R_{27}$-Ser-Arg-Gln-Gln-Gly-Glu-Ser-Asn-Gln-Glu-Arg-Gly-Ala-Arg-Ala-Arg-Leu-A wherein $R_{27}$ is L-Met, L-Nle or L-Leu, A is —OH or —NH$_2$ and the pharmaceutically acceptable non-toxic salts thereof.

9. A compound according to claim 3 which is H-Tyr-D-hArg(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-$R_{27}$-Asn-Arg-Gln-Gln-Gly-Glu-Arg-Asn-Glu-Glu-Gln-Gly-Ala-Lys-Val-Arg-Leu-A wherein $R_{27}$ is L-Met, L-Nle or L-Leu, A is —OH and —NH$_2$ and the pharmaceutically acceptable non-toxic salts thereof.

10. A compound according to claim 3 which is H-Tyr-D-hArg(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-$R_{27}$-Ser-Arg-Gln-Gln-Gly-Glu-Arg-Asn-Gln-Glu-Gln-Gly-Ala-Arg-Val-Arg-Leu-A wherein $R_{27}$ is L-Met, L-Nle or L-Leu, A is —OH or —NH$_2$ and the pharmaceutically acceptable non-toxic salts thereof.

11. The compound of claim 3 is H-His-D-hArg(Et$_2$)-Asp-Ala-Ile-Phe-Thr-Ser-Ser-Tyr-Arg-Arg-Ile-Leu-Gly-Gln-Leu-Tyr-Ala-Arg-Lys-Leu-Leu-His-Glu-Ile-Met-Asn-Arg-Gln-Gln-Gly-Glu-Arg-Asn-Gln-Glu-Gln-Arg-Ser-Arg-Phe-Asn-OH and the pharmaceutically acceptable non-toxic salts thereof.

12. A compound according to claim 3 which is H-Tyr-D-hArg(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-A wherein A is —OH or —NH$_2$ and the pharmaceutically acceptable non-toxic salts thereof.

13. A compound according to claim 3 which is H-Tyr-D-hArg(Et$_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH$_2$ and the pharmaceutically acceptable non-toxic salts thereof.

14. A compound according to claim 3 which is H-Tyr-D-Arg-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH$_2$ and the pharmaceutically acceptable non-toxic salts thereof.

15. A compound according to claim 3 which is H-Tyr-D-hArg(Bu$_2$)-Asp-Ale-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH$_2$ and the pharmaceutically acceptable non-toxic salts thereof.

16. A compound according to claim 3 which is D-hArg(Et$_2$)-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-NH$_2$ and the pharmaceutically acceptable non-toxic salts thereof.

17. A compound according to claim 3 which is H-Tyr-D-hArg($CH_2CH_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-$NH_2$ and the pharmaceutically acceptable non-toxic salts thereof.

18. A compound according to claim 3 which is H-Tyr-D-hArg($CH_2CH_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-$NH_2$ and the pharmaceutically acceptable non-toxic salts thereof.

19. A compound according to claim 3 which is H-Tyr-D-hArg($Et_2$)-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Nle-Ser-Arg-$NH_2$ and the pharmaceutically acceptable non-toxic salts thereof.

20. A pharmaceutical composition comprising a pharmaceutically acceptable excipient and an effective amount of a compound of claim 1.

21. The composition of claim 20 wherein the pharmaceutical composition comprises an implantable extended release formulation.

22. The composition of claim 21 wherein the composition comprises a silastic polymer or a non-toxic polymer hydrolyzable at physiological pH.

23. The composition of claim 22 wherein the polymer is a polylactic/polyglycolic acid polymer.

24. A method of regulating the release of growth hormone which comprises administering to a warm-blooded animal or cold blooded animal in aquaculture an amount of a compound of claim 1 sufficient to stimulate the release growth hormones, either alone or in combination with a pharmaceutically acceptable excipient.

25. A method in accordance with claim 24 wherein said a warm-blooded animal is a mammal.

26. A method in accordance with claim 24 wherein said a cold-blooded animal is a fish.

* * * * *